(12) United States Patent
Themis

(10) Patent No.: US 11,567,064 B2
(45) Date of Patent: Jan. 31, 2023

(54) METHOD OF PREDICTING THE LIKELIHOOD OF SUCCESS OF GENE THERAPY

(71) Applicant: BRUNEL UNIVERSITY LONDON, Middlesex (GB)

(72) Inventor: Michael Themis, Middlesex (GB)

(73) Assignee: BRUNEL UNIVERSITY LONDON, Middlesex (GB)

( * ) Notice: Subject to any disclaimer, the term of this patent is extended or adjusted under 35 U.S.C. 154(b) by 855 days.

(21) Appl. No.: 16/330,362

(22) PCT Filed: Sep. 27, 2017

(86) PCT No.: PCT/GB2017/052888
§ 371 (c)(1),
(2) Date: Mar. 4, 2019

(87) PCT Pub. No.: WO2018/060697
PCT Pub. Date: Apr. 5, 2018

(65) Prior Publication Data
US 2021/0285934 A1 Sep. 16, 2021

(30) Foreign Application Priority Data
Sep. 28, 2016 (GB) ..................... 1616470

(51) Int. Cl.
*G01N 33/50* (2006.01)
(52) U.S. Cl.
CPC ..... *G01N 33/5041* (2013.01); *G01N 33/5035* (2013.01); *G01N 2800/52* (2013.01)
(58) Field of Classification Search
CPC ........... G01N 33/5041; G01N 33/5035; G01N 2800/52
See application file for complete search history.

(56) References Cited

FOREIGN PATENT DOCUMENTS

WO   WO 03/097842     11/2003
WO   WO 2013/186398   12/2013

OTHER PUBLICATIONS

Porteus Molecular and Cellular Biology 2003 vol. 23, p. 3558-3565 (Year: 2003).*
Hingorani et al., "Therapeutic Effect of Sodium Iodide Symporter Gene Therapy Combined With External Beam Radiotherapy and Targeted Drugs That Inhibit DNA Repair", Molecular Therapy, 2010, 18(9): 1599-1605.
Reja, "A study of mechanisms of genotoxicity in mammalian cells by retrovirus vectors intended for gene therapy", thesis submitted for the degree of Doctor of Philosophy, Biosciences, School of Health Sciences and Social Care, Brunel University, Sep. 2013.
Cheng et al., "The yield of DNA double strand breaks determined after exclusion of those forming from heat-labile lesions predicts tumor cell radiosensitivity to killing", Radiotherapy and Oncology, 2015, 116: 366-373.
Clingen et al., "Histone H2AX phosphorylation as a molecular pharmacological marker for DNA interstrand crosslink cancer chemotherapy", Biochemical Pharmacology, 2008, 76: 19-27.
Daniel et al., "Evidence that Stable Retroviral Transduction and Cell Survival following DNA Integration Depend on Components of the Nonhomologous End Joining Repair Pathway", Journal of Virology, 2004, 78(16): 8573-8581.
Dolan et al., "Integrated Stochastic Model of DNA Damage Repair by Non-homologous End Joining and p53/p21-Mediated Early Senescence Signalling", PLoS Computational Biology, 2015, 11(5): e1004246.
Federico et al., "Chromosomal Integrity after UV Irradiation Requires FANCD2-Mediated Repair of Double Strand Breaks", PLoS Genetics, 2016, 12(1): e1005792.
Kroeber et al., "Distinct increased outliers among 136 rectal cancer patients assessed by γH2AX", Radiation Oncology, 2015, 10:36, 1-7.
Lau et al, "Suppression of retroviral infection by the RAD52 DNA repair protein", The EMBO Journal, 2004, 23:3421-3429.
Mumbrekar et al., "Influence of Double-Strand Break Repair on Radiation Therapy-Induced Acute Skin Reactions in Breast Cancer Patients", International Journal of Radiation Oncology Biology Physics, 2014, 88: 671-676.
Podhorecka et al., "H2AX Phosphorylation: Its Role in DNA Damage Response and Cancer Therapy", Journal of Nucleic Acids, 2010, 2010: 1-9.
Quarnstrom et al., "DNA double strand break quantification in skin biopsies", Radiotherapy and Oncology, 2004, 72: 311-317.
Sinn et al., "Gene Therapy Progress and Prospects: Development of Improved lentiviral and retroviral vectors—design, biosafety, and production", Gene Therapy, 2005, 12: 1089-1098.
Skalka et al., "Retroviral DNA integration and the DNA damage response", Cell Death and Differentiation, 2005, 12: 971-978.

* cited by examiner

*Primary Examiner* — Changhwa J Cheu
(74) *Attorney, Agent, or Firm* — James S. Keddie; Bozicevic, Field & Francis LLP

(57) ABSTRACT

A method of predicting the likelihood of success of a gene therapy procedure includes inducing DNA damage in a cell sample from an individual. The ability of the individual's cells in the sample to repair the DNA damage is then assessed to determine whether the individual could tolerate DNA damage caused by a gene therapy vector. In preferred embodiments, the ability of the individual's cells to repair DNA damage is assessed by detecting, and monitoring the subsequent disappearance of, a marker of DNA damage repair (such as gamma H2AX or phosphorylated 53BP1) in the sample.

21 Claims, 3 Drawing Sheets

METHOD OF PREDICTING THE LIKELIHOOD OF SUCCESS OF GENE THERAPY

CROSS-REFERENCE TO RELATED APPLICATIONS

This application is a § 371 national phase of International Application No. PCT/GB2017/052888, filed on Sep. 27, 2017, which claims the benefit of United Kingdom Application No. 1616470.9, filed on Sep. 28, 2016, which applications are incorporated by reference herein.

The present invention relates to a method of predicting the likelihood of success of gene therapy, wherein the gene therapy procedure involves DNA damage caused by a gene therapy vector. In particular, the gene therapy may use integrating vectors that require DNA damage repair.

Gene therapy intends to provide a healthy, functional gene to produce a product that replaces its abnormal, non-functional counterpart to treat or correct a genetic disease. This may be achieved using non-viral or viral vectors. Vectors can deliver DNA that remains outside a patient's chromosome (episomal) or within a patient's chromosome (integrated). For example, vectors based on retroviruses, lentiviruses and adeno-associated viruses integrate into the host chromosome for permanent gene delivery. Many gene therapy applications use vectors that can integrate (become part of) the target host's genome to achieve permanent delivery of a therapeutic gene.

The discovery that certain genetic disorders are caused by a defective copy of a single gene, along with the development of recombinant DNA technology, led scientists back in the 1960s and 1970s to consider the possibility of treating or curing these genetic diseases by adding a functional copy of the gene into a patient's cells or replacing the defective copy. This has been the goal for several decades, and whilst simple in theory, gene therapy has met with limited practical success. A replacement gene must be effectively delivered to the correct cells in the patient, it needs to be stable such that it is replicated when the cell divides (as indicated above, this may be achieved by integration into the patient's chromosome), and it needs to be expressed so that functional protein is produced where and when required. On top of the hurdles of getting functional gene expression to treat the disease, gene therapy has been found, in some cases, to harm the patient, for example, by causing tumour formation, leukaemia, and other cancers.

The present invention seeks to provide a method of predicting the likelihood of success of a gene therapy procedure in an individual.

According to an aspect of the present invention, there is provided a method of predicting the likelihood of success of a gene therapy procedure in an individual, wherein the gene therapy procedure involves DNA damage caused by a gene therapy vector, the method including: inducing DNA damage in a cell sample from the individual; and assessing the ability of the individual's cells in the sample to repair the DNA damage; for the purpose of determining whether the individual could tolerate DNA damage caused by a gene therapy vector.

This method enables determination of successful delivery of nucleic acid to the genome of the target cell and thus prediction of the likelihood of harm to an individual to be exposed to a gene therapy vector that causes DNA damage. The method thus enables a prediction of whether or not a gene therapy procedure would be safe for that individual.

The gene therapy procedure may involve integration of exogenous nucleic acid into the individual's genome.

The DNA damage in the gene therapy procedure may be caused by integration of exogenous nucleic acid into the individual's genome The DNA damage may be induced in the assay by a gene therapy vector, which in certain embodiments may be a virus.

The ability of the individual's cells in the sample to repair the DNA damage may be assessed by detecting the presence of one or more proteins involved in DNA damage repair in the sample.

Assessing the ability of the individual's cells in the sample to repair the DNA damage may include detecting a modification, such as phosphorylation, of one or more proteins involved in DNA damage repair in the sample.

The proteins or the modification of the proteins may be detected using an antibody-based method, such as immunocytochemistry.

The detecting is preferably carried out at more than one time point to create a DNA repair profile for the individual.

The detecting may be carried out at one or more, for example, two, three, four, five, six, seven or more of the following time points: 0 minutes, 5 minutes, 30 minutes, 1 hour, 6 hours, 12 hours, 24 hours, 48 hours, and 72 hours after infection, in any combination. The detecting may be carried out all of these time points.

The detecting may include obtaining a measurement of the amount of protein or modified protein present at each time point.

The amount of protein or modified protein present may be determined by determining the number of foci in the nucleus in the cell sample.

Assessing the ability of the individual's cells in the sample to repair the DNA damage may include detecting the presence of a marker of DNA damage repair, such as gamma H2AX and/or phosphorylated 53BP1.

The sample may include T cells from the individual.

Embodiments of the present invention are described below, by way of example only, with reference to the accompanying drawings, in which.

Figure 1:
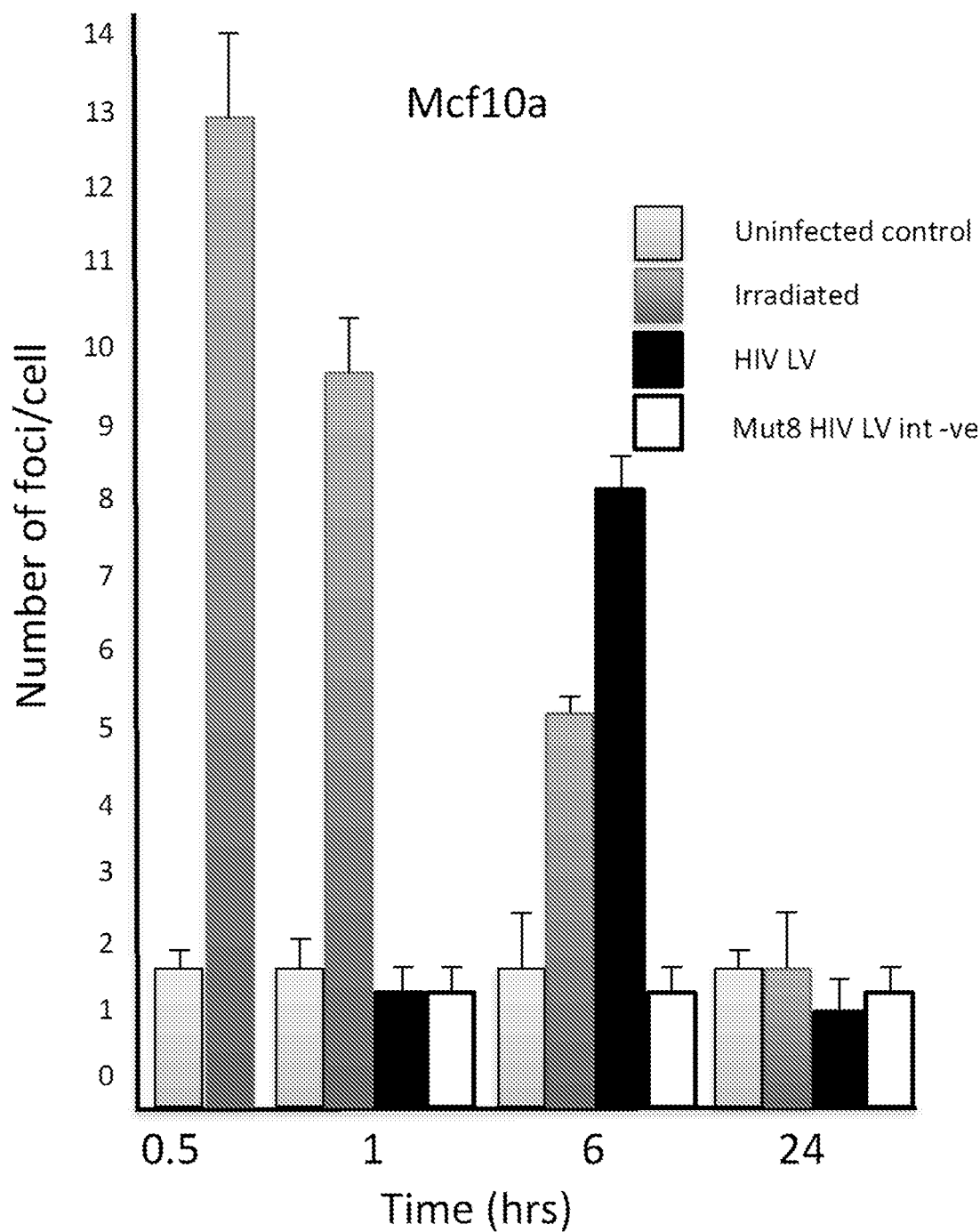
FIG. 1 shows a DNA repair profile in cells with a proficient DNA damage repair pathway.

Embodiments of the present invention provide a predictive safety assay that can be used to inform an individual whether or not they have the ability to protect themselves from DNA damage caused by a gene therapy vector, thereby enabling the individual and healthcare professionals to make an informed choice regarding whether or not to undergo gene therapy.

By way of example, human immunodeficiency virus has been modified to be able to deliver genes to cells followed by integration of the virus (vector) into the host genome. This provides permanent delivery of the vector into the genome of the target host. These vectors have been engineered to do this and do not replicate thereafter to provide safe gene transfer. The vector is engineered to carry a gene that can treat or correct a disease where the same gene is present in the host but is mutated, thereby causing the genetic disease. Gene therapy involves adding the normal or non-mutated gene.

During the infection process, the DNA carrying molecule or virus enters the cell. The DNA carrying molecule or virus has a protein that cuts open the cell's genomic DNA and inserts the DNA carrying molecule or virus genome into where the cut has been made. To integrate DNA, the vector will usually use its own integrase enzyme that cuts the host DNA and then inserts the therapeutic 'foreign' DNA. To complete this process, the host cell's proteins complete the unfinished repair resulting in integration of the DNA or virus genome into the host permanently. The repair process requires the cell to identify broken or damaged DNA as a double strand break. The cell then recruits a number of repair proteins and alters local proteins at the break site in order to signal the host to send the repair proteins to the breaks and repair them. For example, histone H2AX and 53BP1 are proteins that are phosphorylated when DNA damage is detected. They are subsequently dephosphorylated as the damage is repaired.

This DNA damage repair process is called the non-homologous end-joining pathway (NHEJ). If gene therapy were applied to patients that cannot repair this damage they may develop cancer due to genome damage. The assay described in this patent application measures the breakage profile from DNA breakage to DNA repair. It shows whether or not the host is able to make this repair and predicts whether a patient can tolerate gene therapy safely. A functioning DNA damage repair pathway is thus required for successful integration of foreign DNA into a host genome (Daniel et al. (2004); Lau et al. (2004); Mumbrekar et al. (2014); Federico et al. (2016)).

To date, there has been no pre-screen to determine whether a patient is capable of performing the NHEJ pathway before gene therapy. If even one of the several enzymes in this pathway is mutated in the intended patient then gene therapy using integrating DNA carrying molecules or viruses would cause damage (mutation) to the host DNA that may result in cancer and even death.

The present predictive safety assay is used to determine whether or not a subject can repair DNA damage caused, in particular, by a gene therapy vector (usually plasmid DNA or a virus), which during its natural life cycle breaks the target host DNA to insert itself into the target cell genome (integration) thus achieving permanent residence into the host DNA.

The DNA repair process is natural to the individual's cells but may not be available to that individual as a result of mutation of a gene involved in the repair process or loss as a result of disease. The assay measures an individual's ability to repair DNA.

Assays to test whether DNA damage is capable of being repaired are known. However, these have not been applied or offered to individuals in a personalised manner as a predictive assay to assess the ability to repair DNA damage caused by exposure to gene therapy vectors. In most cases individuals have the capability to repair their DNA. However, some individuals are not fully capable of this repair as they are impaired in or lack the essential natural process to repair damaged DNA in their cells, and there is a need to inform them of this risk. The outcome of this risk is well known and is understood to involve steps to neoplasm. Importantly, the assay would identify individuals that can tolerate gene therapy to treat or correct genetic disease. Embodiments of the present invention make such an assay available, specifically for the purpose of making individuals aware of the risk of DNA damage if they were to be treated by gene therapy vectors.

In an embodiment, the steps in the test involve measuring a subject's ability to repair their DNA as follows:

1. Isolation of Cells from an Individual

Before carrying out the assay, a sample of cells or tissue from the patient needs to be obtained. The cells can be obtained from a blood sample or any other part of the body, and is a routine procedure. Whilst straightforward, in practice this would be carried out by a healthcare professional. In one example, a sample of T cells is obtained for the assay.

2. Routine Cell Culture

The cells should be cultured using standard procedures well known to the person skilled in the art prior to exposure to a DNA damaging agent such as an integrative gene therapy virus. The cell culture enables enough cells to be infected in order that measurement of an agent indicating DNA damage has occurred followed by repair and loss of these indicators occurring over time (0.5 hours-72 hours usually) can be obtained. Usually between 1000-1,000,000 cells are required for immune-detection.

3. Application of DNA Damaging Agent to the Individual's Cells.

Once the cells have reached the required number or confluence/density, an agent is applied to cause damage to the DNA. Any DNA damaging agent may be used in the assay, such as: a gene therapy vector, radiation, for example, UV light or a chemical such as benzo(a)pyrene. In preferred embodiments, the DNA damaging agent is a gene therapy vector, such as a virus that uses a DNA cleavage enzyme such as an integrase. Examples of possible viruses are retroviruses such as the Moloney murine leukaemia virus (MLV) or lentiviruses such as the human immune-deficiency virus (HIV) or adeno-associated viruses (AAV). The skilled person will appreciate that other viruses may also be suitable. However, as these may be expensive to produce, in other embodiments cheaper DNA damaging agents such as radiation or chemical agents may be used.

Virus can be obtained commercially or grown in the laboratory by a person skilled in the art. DNA damaging agents such as chemicals can be obtained commercially. UV light or irradiation requires a light source or a radiation source such as a cobalt source to generate damaging radiation.

Other possible DNA damaging agents will be known to the skilled person.

4. Detection of Proteins Involved in DNA Damage Repair

DNA damage may be performed on adherent cells or suspended cells (such as T cells). Sets of cells are prepared for each time point at which DNA damage and repair is to be measured. Usually time points depend on the agent used. In the case of viruses preferred time points might be: Time 0, 6, 12, 24, 48 and 72 hours. For chemicals or radiation, time points might be: 0, 0.5, 6, 12, 24, 48 and 72 hours.

After DNA damaging agent has been applied to the sample of the patient's cells, the assay detects presence of proteins involved in DNA damage repair. Preferred embodiments detect biomarkers of DNA damage, to provide a repair profile for the individual. These biomarkers may be phosphorylated histone H2AX (gamma H2AX) or phosphorylated 53BP1. This provides an indication of whether or not the DNA damage repair pathway is functional in the individual.

Detection of these proteins can be done using techniques well known to the skilled person. For example, fixing and immunocytostaining of the individual's cells or immunohistochemistry on tissue biopsies taken from the individual can be used to detect the presence of proteins involved in DNA damage repair.

5. Measurement of DNA Damage Repair Proteins

By measuring the emergence and disappearance of the DNA damage repair proteins over time, an assessment can be made as to whether the repair pathway is functional. In the case of detecting gamma H2AX or phosphorylated 53BP1, an individual with a functional repair pathway should show emergence and subsequent disappearance of these phosphorylated proteins. An individual with an impaired repair pathway would show emergence of the proteins, but the phosphorylation would remain as time goes by, as the DNA damage is not repaired.

The assay measures the profile of DNA repair using immune-detection or simply a measurement of the repaired DNA over time to show a normal repair profile. This would be compared to standards that display a normal repair phenotype. The assay may thus be carried out in parallel on cells known to have an intact NHEJ pathway. Suitable controls such as uninfected patient cells and a cell line proficient in NHEJ may be included in the assay.

DNA damage repair assays that show the ability of an individual to repair DNA damage before treatment by gene therapy vectors have yet to be applied as a predictive safety test in a personalised manner. Such a test would be beneficial to individuals before undergoing such procedures. By applying the established assays to individual's cells in a personalised manner the predictive test enables personal choice to be made on whether or not to accept gene therapy that could potentially cause harm.

Embodiments of the present invention concern a test based on DNA damage repair where the repair proteins are used. These molecules become altered when DNA is damaged and their activity is lost once repair has taken place. The test enables monitoring of DNA damage and repair after vector infection of cells. The profile obtained demonstrates whether the host-infected cells can perform the repair. Once applied to patient T cells for example, this assay will provide a read-out on the safety or 'eligibility' of the patient to have safe gene transfer using integrating vectors.

Use of the assay described in the present application will help to prevent harm to patients exposed to DNA damage or gene therapy vectors, leading to more positive clinical outcomes and saving health services money in treating patients that would otherwise have been harmed. Furthermore, it should lead to a reduction in the use of animal experiments to study gene therapy safety.

It is envisaged that the assay may be streamlined to be performed in kit form. Hence, the assay could take advantage of immuno-detection via a 'dip-stick' for the presence and removal of DNA repair proteins indicating the process of DNA repair has been completed by the cell.

EXAMPLE 1—DETERMINING A DNA REPAIR PROFILE FOR CELLS WITH AND WITHOUT A PROFICIENT DNA DAMAGE REPAIR PATHWAY

Cell Culture

Figure 2:
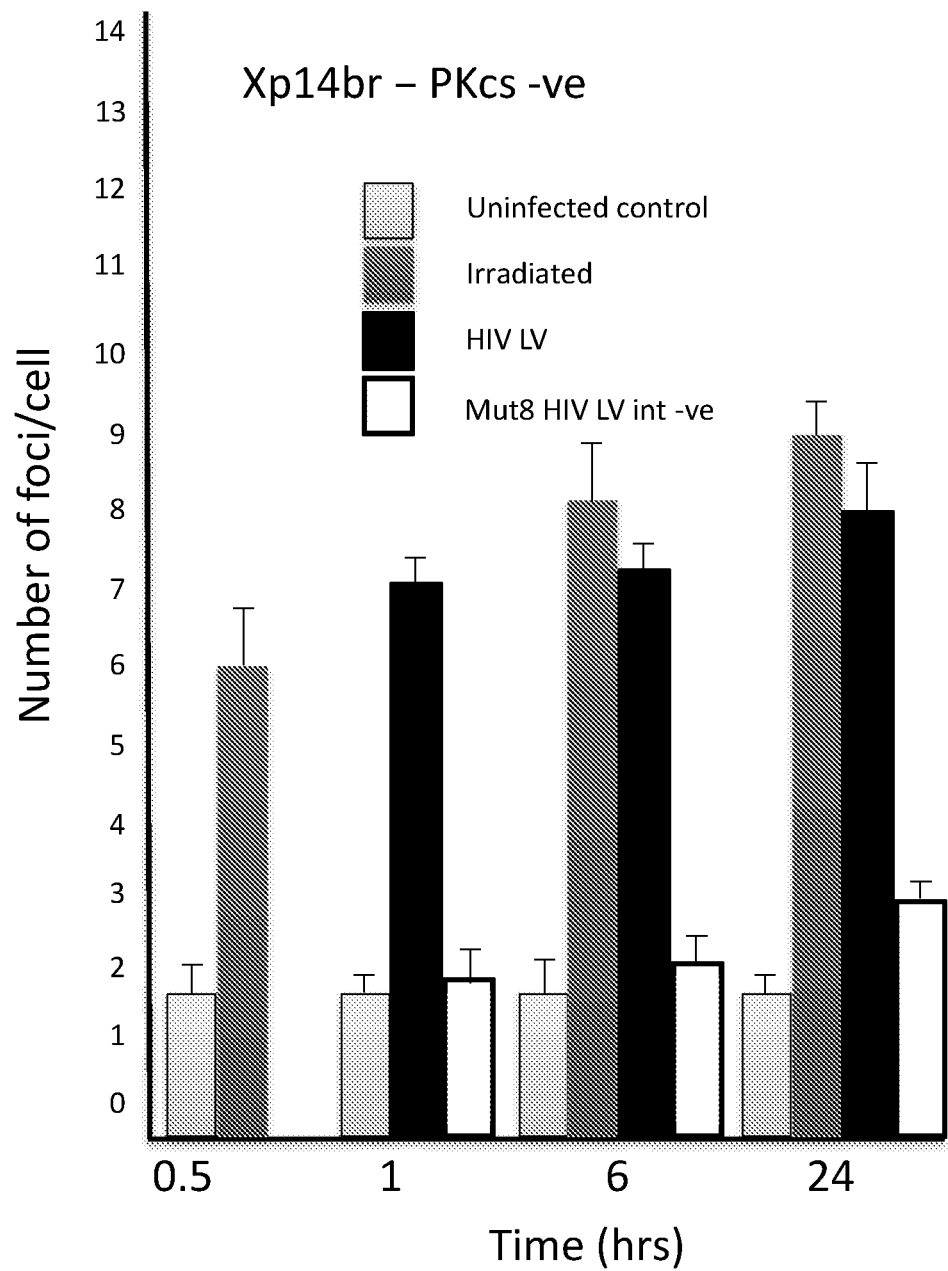
FIG. 2 shows a DNA repair profile in cells without a proficient DNA damage repair pathway.

Cells to be exposed to a DNA damaging agent (in practice, cells from a patient sample) were grown in complete medium supporting their growth. In this case, the adherent cell lines shown in FIGS. 1 and 2 are Mcf10a (repair proficient) and Xp14br (non-repair proficient) respectively. For the adherent cells, Dulbecco's Modified Eagle Medium (DMEM) with 10% FBS, with or without antibiotics was used. The cells were grown as monolayers in 92 mm plastic culture dishes in an incubator maintained at 37° C. with 5% $CO_2$ and a 95% air atmosphere humidified environment.

Once the cells reached 80% confluence, the culture medium was aspirated with a glass Pasteur pipette followed by washing with phosphate buffered saline (PBS) at 37° C. to remove dead cell debris. This provides healthy dividing cells to be subjected to DNA damage.

Exposure of Cells to DNA Damage Agents

Either adherent or suspension culture cells (such as T cells) may be used in the assay. As indicated above, adherent cells were used in this Example The adherent cells, were transferred from tissue culture plates after trypsinisation to Polyprep slides by transfer of 1 ml cell suspension from 70% or 100% confluency and left to grow overnight before exposure to the DNA damaging agent the next day. (For suspension culture cells, exposure would be carried out in tubes where cells exist in suspension.)

Cells were exposed to DNA damage by infecting with a replication defective HIV gene therapy vector for 6-12 hours or were irradiated for the desired time (approximately 0.5-1 hour). After exposure, DNA damaged cells were taken at time points of 0.5, 1, 6 and 24 hours to assess DNA damage or repair using immuno-detection after fixation of the cells.

Fixation for Immunocytochemistry $1 \times 10^3$ target cells exposed to DNA damaging agents were then transferred to slides. (Cells in suspension would be treated in tubes.) The fixing process involved aspirating the culture medium. The slides were then placed in 5 ml of 4% formaldehyde and 45 ml of PBS and left for 15 minutes. Following this the cells were removed and placed in PBS at 4° C. until immune-detection was carried out.

For cells in suspension, fixing would involve centrifugation of suspension culture cells at 1200 g and replacing this with ice chilled PBS, which is then aspirated or removed after centrifugation. The cells in tubes would then be placed in formaldehyde/PBS as described above.

Gamma H2AX Staining for Immunocytochemistry

After fixation, 0.2% Triton™ X-100 was used to permeabilise cells for 10 minutes at 4° C. followed by the addition of blocking buffer (0.1 g BSA in 50 µl Triton™ X-100 and 50 ml PBS) to block for 1 hour. Cells on slides were then incubated with primary antibody solution consisted of an anti-phospho-histone H2AX (serine 139), mouse monoclonal IgG1 antibody (1:1,000) in blocking buffer. Excess primary antibody was removed by washing three times for 5 minutes in TBST solution (8.8.grams of NaCl+0.2 grams of KCl+3 grams of Tris base+500 µl Tween 20 in 1 litre of $dH_2O$, pH 7.4), followed by incubation for 1 hr at room temperature in a secondary antibody solution consisting of an Alexa Fluor® 488 rabbit anti-mouse IgG antibody (1:1000) in blocking buffer. Cells were washed three times for 5 minutes in TBST and then three times for 5 minutes in PBS before being de-hydrated in ethanol (70%, 90% and 100%) for 3 minutes each time on slides. After air drying 15 µl of mounting medium containing DAPI was added to each slide and covered with a cover slip (Fisher Scientific) and sealed using clear nail varnish. Image acquisition was performed at room temperature using a Zeiss Axioplan 2 microscope equipped with a ×100 ZEISS Plan-NEOFLUAR 1.3 Oil objective lens and a Zeiss Axiocam colour camera under the control of AXIOVISION 4.2 software.

Detection of DNA Repair

The number of foci per cell/nucleus that appeared stained by the antibodies was counted and plotted using appropriate statistical software to represent DNA damage. Staining was continued on cells after exposure at several desired time points after DNA damage as shown in FIGS. 1 and 2 to profile DNA damage and repair by the emergence and disappearance of gamma H2AX.

DNA damage was measured using immunocytochemistry of the gamma H2AX histone (as a representative molecule of one of the proteins involved in the DNA damage repair pathway) that becomes phosphorylated upon DNA damage from its H2AX unphosphorylated form. Following DNA repair, the protein becomes de-phosphorylated and therefore not detectable. Hence, over time 0.5-72 hours, repair can be monitored. FIG. 1 represents Mcf10a cells capable of DNA damage repair via the NHEJ pathway. FIG. 2 represents Xp14br cells that are mutated in the PKcs gene responsible for DNA repair and are therefore impaired for repair.

FIG. 1 shows the results for Mcf10a cells that are proficient in DNA damage repair. The DNA damaging agents used were irradiation (dark grey bars), and a gene therapy attenuated HIV LV (black bars). Controls include uninfected cells (light grey bars) and Mut8 HIV LV that has a mutated integrase not able to cause DNA damage but still able to infect cells (white bars).

FIG. 1 shows that, there is no increase in gamma H2AX foci in cells not exposed to DNA damaging agents. Cells that are exposed to irradiation show at 0.5 hours an increase in foci representing DNA damage that over time is repaired as shown by the disappearance of foci by 24 hours. For cells that are infected with virus, DNA damage occurs at the later time point of 6 hours and repair appears complete, again by 24 hours.

FIG. 2 shows the results for DNA damage repair deficient cells Xp14br (PKcs mutated) cells. FIG. 2 shows that, irradiation of cells causes DNA damage but this is not repaired over by the 24 hour time point.

This is also true for the virus-infected cells. Interestingly, for unknown reasons infection of the DNA damage repair deficient cells appears to cause DNA damage at the earlier time point of 1 hour.

If there are no positively stained foci remaining, this demonstrates that DNA damage has disappeared and repair is complete. This would be expected to take 48-72 hours in general. These data illustrate that if an individual is not proficient in DNA damage repair then their DNA would remain unrepaired and damaged and this can lead to cancer.

Experiments were also carried out using AT5BIVA cells deficient in the DNA repair enzyme ATM. The results (not presented here) were very similar to those shown in FIG. 2.

Additionally/alternatively to gamma H2AX, other DNA damage repair proteins could be detected and measured, an example being the emergence of phosphorylated and de-phosphorylated 53BP1 DNA repair protein.

In practice, preferred cells taken from a patient's blood sample might be T cells. These do not require attachment to the substratum of a tissue dish and could be grown in suspension in a medium supporting their growth in Gibco CTS cell media. The skilled person could readily adapt the protocol above for use on cells grown in suspension.

Other modifications would be apparent to the skilled person.

EXAMPLE 2—MEASUREMENT OF β-GALACTOSIDASE EXPRESSION AND CELL SURVIVAL

Evidence that intact DNA damage/repair pathways enable successful gene transfer and cell survival during and after infection can be obtained by measuring the difference in successful gene expression and cell survival of cells subjected to infection by gene therapy vectors. The gene carried by the vector can be shown to be expressed using a number of routine assays (such as by immunostaining, or chemical colour change for the presence of the protein produced from gene expression, or measurement of RNA production by the gene carried by the vector). An example of such an assay is staining for the presence of β-galactosidase activity as a result of gene transfer of the β-galactosidase gene. Cell survival can be measured by exclusion of a marker dye such as methylene blue only by healthy cells and not by dying or dead cells.

12 well plates were seeded with 1.5 or $2.0 \times 10^5$ cells/ml respectively and left at 37° C. until the cells reattached. An appropriate dilution series of the vector to be used was added to growth medium so that multiplicities of infection (ratio of vector to cells) ranged from 1-1000 using either concentrated vector or vector supernatants from virus producer cells. Growth medium was then removed from the wells and replaced with $3 \times 1.0$ ml volumes (12-well plates) of the appropriate viral dilutions. Several wells per plate were left uninfected to serve as negative controls. Plates were replaced at 37° C. for 48 hours to allow infection and β-galactosidase reporter gene expression to proceed.

After 48 h the medium was aspirated and the cells gently washed with warm PBS. The cell monolayers were fixed by immersion in cell fixing solution (PBS with 2% formaldehyde and 7% glutaraldehyde) for 15 minutes at room temperature, washed once more with PBS, then stained with pre-prepared X-Gal solution overnight (at room temperature, protected from light). The X-Gal compound is a chromogenic substrate of β-galactosidase, and hydrolysis of the β-1,4 bond between galactose and the 5-bromo-4-chloro-3-indolyl parts of the molecule results in the production of an insoluble blue precipitate. The distribution of any β-galactosidase enzyme within the sample is therefore revealed by the appearance of blue pigment.

To count cells, X-Gal staining solution was aspirated and replaced with PBS. Plates were viewed on an Olympus CK40 inverted light microscope fitted with a movable specimen guide, and the wells inspected to find the most informative viral dilution for counting. Ideally the dilution counted should contain approximately 50-500 blue cells per well. Doublets and triplets of cells, resulting from the division of single infected cells during the 48 h assay, were counted as single positive events. The numbers of blue cells in each well counted are recorded using a tally counter, and all wells from each dilution were averaged.

To measure cell survival, cell counting was performed using either a glass haemocytometer or the Invitrogen Countess. The Countess is limited by its measurement range ($1 \times 10^4$-$1 \times 10^7$ cells/ml), therefore if cell concentrations were below this, then a traditional Neubauer glass haemocytometer was used instead. When counting cells using the haemocytometer, cells were detached from petri dishes using 1 ml of trypsin. Once cells were detached, they were recovered in 10 ml of complete medium. Ten microlitres of the cell suspension was added to 10 µl of Trypan blue to allow for exclusion of dead cells from the cell count. Ten microlitres of the cell suspension mixed with the Trypan blue was loaded onto a glass haemocytometer and cell counts were performed at 20× magnification using an Olympus CK2 microscope.

Cell viability assays used the haemocytometer and a dye, such as trypan blue, which gives a quantitative standard for the viability of the cells. Cells that exclude trypan blue are considered viable, whereas cells that take up the dye are dead. To perform this, cells were first detached with 1 ml of 1× trypsin-EDTA and a cell suspension was made with 1 ml of DMEM medium. Next, 100-200 µl of cell suspension was taken into a fresh microcentrifuge tube and an equal volume of 0.4% (w/v) trypan blue was added, and mixed well by pipetting up and down. Cells were counted using a haemocytometer, and their viability as a percentage was determined by the calculating the ratio of viable cells to the total number of cells×100.

To show that cells with an intact DNA repair pathways provide for gene transfer and that cells with impaired DNA repair do not support successful gene transfer to the level of intact DNA repair pathway cells, the infected cells were subjected to assays that provide evidence of successful gene transfer by way of positive expression of the gene being transferred by the vector.

Figure 3:
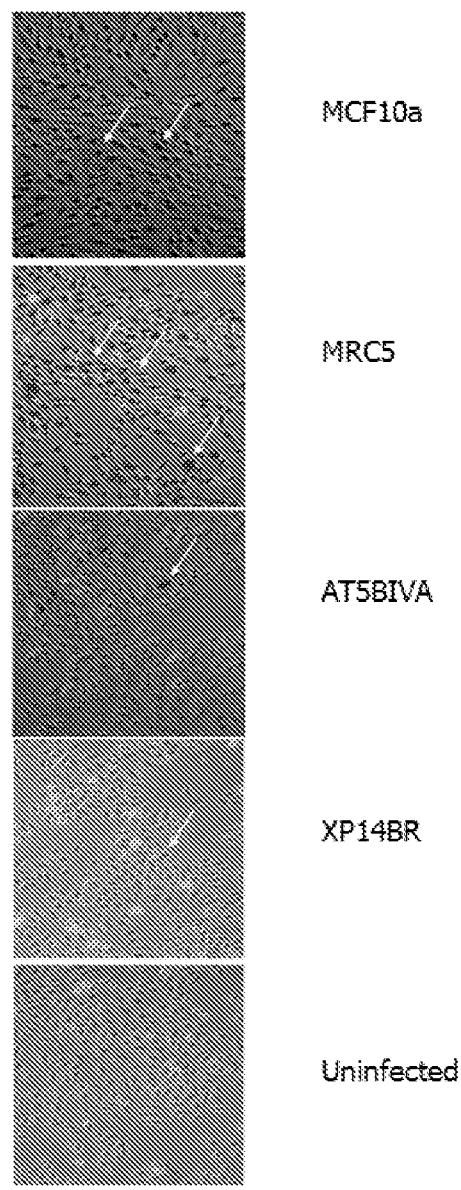
FIG. 3 shows the results of staining for β-galactosidase activity in cells with and without a proficient DNA damage repair pathway.

FIG. 3 shows that cells infected with a retrovirus (Moloney murine leukaemia virus) carrying the β-galactosidase gene were positively infected by their dark appearance as a result of staining for the presence of β-galactosidase gene expression (white arrows). This level can be counted under microscopy to provide a measure of successful infection and gene transfer. Images were taken at ×100 magnification using a Zeiss Axiovert 25 microscope. In this example, MCF10a and MRC5 cells have an intact DNA damage/repair pathway, whereas AT5BIVA and XP14BR cell do not.

The results are presented in Table 1, below.

TABLE 1

| Cell Line | LV Vector (% infection) | Cell Survival (% post LV infection - 72 hrs) | RV vector (% infection) | Cell Survival (% post RV infection - 72 hrs) |
| --- | --- | --- | --- | --- |
| MCF10a | 68+/−4 | 82+/−6 | 99+/−1 | 87+/−6 |
| MRC5 | 43+/−6 | 85+/−6 | 100+/−5 | 75+/−6 |
| AT5BIVA | 9+/−5 | 44+/−2 | 10+/−5 | 22+/−2 |
| XP14BR | 27+/−3 | 46+/−2 | 5+/−7 | 27+/−6 |

Table 1 shows infection and survival levels for infected and control uninfected Mcf10a, MRC5, AT5BIVA and Xp14BR cells 72 hours after treatment. Cells were infected with a retrovirus (MLV) or a lentivirus (LV). Both MCF10a and MRC5 cells with intact DNA damage/repair pathways show high levels of successful infection (after counting positive β-galactosidase gene expressing cells) and the survival of these cells. AT5BIVA and XP14BR cells with mutated DNA damage/repair pathways had significantly reduced levels of infection and survival. The data show that with intact DNA damage/repair pathways both successful gene delivery and cell survival can be predicted, whereas for cells with mutated DNA damage/repair pathways when exposed to retrovirus or lentivirus infection, low level infection leading to successful gene expression and high level cellular toxicity is predicted.

The results obtained in Example 2 demonstrates that the DNA damage/repair assay (for example, as described in Example 1) can be used to predict successful DNA transfer and cell survival using assays that show the difference of this success in cells with and without intact DNA repair pathways All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in United Kingdom patent application 1616470.9, from which this application claims priority, and in the abstract accompanying this application are incorporated herein by reference.

REFERENCES

Daniel et al. (2004) *J. Virol.* 78, 8573-8581.
Lau et al. (2004) *EMBO J.* 23, 3421-3429.
Mumbrekar et al. (2014) *Int. J. Radiat. Oncol. Biol. Phys.* 88, 671-676.
Federico et al. (2016) *PLoS Genet* 12, e1005792.

The invention claimed is:

1. A method of performing a gene therapy procedure in an individual, wherein the gene therapy procedure involves DNA damage caused by the retrovirus and integration of exogenous nucleic acid into the individual's genome, the method including:
    inducing DNA damage in the form of a double strand break in a cell sample from the individual using a retrovirus;
    assessing the ability of the individual's cells in the sample to repair the double strand breaks to determine whether the individual has the capability to repair double strand breaks in their DNA;
    identifying the individual as capable of repairing double strand breaks in their DNA; and
    administering the gene therapy to the individual.

2. The method of claim 1, wherein assessing the ability of the individual's cells in the sample to repair the DNA damage includes detecting a marker of DNA damage repair in the sample.

3. The method of claim 1, wherein assessing the ability of the individual's cells in the sample to repair the DNA damage includes detecting a modification of one or more proteins in the sample.

4. The method of claim 3, wherein the modification is phosphorylation.

5. The method of claim 2, wherein the marker is detected using an antibody-based method.

6. The method of claim 2 wherein the detecting is carried out at more than one time point to create a DNA repair profile for the individual.

7. The method of claim 2, wherein the detecting is carried out at least one of the following time points: 0 minutes, 5 minutes, 30 minutes, 1 hour, 6 hours, 12 hours, 24 hours, 48 hours, and 72 hours after the retrovirus infection.

8. The method of claim 2, wherein the detecting includes obtaining a measurement of the amount of marker present at each time point.

9. The method of claim 8, wherein the amount of marker present is determined by determining the number of foci per nucleus in the cell sample.

10. The method of claim 1, wherein assessing the ability of the individual's cells in the sample to repair the DNA damage includes detecting the presence of gamma H2AX.

11. The method of claim 1, wherein assessing the ability of the individual's cells in the sample to repair the DNA damage includes detecting the presence of phosphorylated 53BP1.

12. The method of claim 10, wherein assessing the ability of the individual's cells in the sample to repair the DNA damage includes monitoring the subsequent disappearance of gamma H2AX.

13. The method of claim 1, wherein the sample includes blood cells from the individual.

14. The method of claim 3, wherein the modification of the proteins is detected using an antibody-based method.

15. The method of claim 3, wherein the detecting is carried out at more than one time point to create a DNA repair profile for the individual.

16. The method of claim 3, wherein the detecting is carried out at least one of the following time points: 0 minutes, 5 minutes, 30 minutes, 1 hour, 6 hours, 12 hours, 24 hours, 48 hours, and 72 hours after infection.

17. The method of claim 3, wherein the detecting includes obtaining a measurement of the amount of modified protein present at each time point.

18. The method of claim 17, wherein the amount of modified protein present is determined by determining the number of foci per nucleus in the cell sample.

19. The method of claim 11, wherein assessing the ability of the individual's cells in the sample to repair the DNA damage includes monitoring the subsequent disappearance of phosphorylated 53BP1.

20. The method of claim 1 including the step of assaying for successful expression of a transgene carried by the retrovirus.

21. The method of claim 20, wherein the transgene encodes β-galactosidase.

\* \* \* \* \*